United States Patent
Hobson et al.

(10) Patent No.: US 6,274,370 B1
(45) Date of Patent: Aug. 14, 2001

(54) YEAST DEBRIS PRODUCTS

(75) Inventors: John Charles Hobson, Burton-on-Trent; Roderick Norman Greenshields, West Glamorgan, both of (GB)

(73) Assignee: Corn Products International, Inc., Bedford Park, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/895,383

(22) Filed: Jul. 16, 1997

Related U.S. Application Data

(62) Division of application No. 08/470,386, filed on Jun. 6, 1995, now Pat. No. 5,686,296, which is a division of application No. 08/047,726, filed on Apr. 15, 1993, now Pat. No. 5,545,557.

(30) Foreign Application Priority Data

Apr. 16, 1992 (GB) .................................................. 9208371

(51) Int. Cl.[7] .............................. C12N 1/14; C12N 1/16; C12N 1/18; C12P 1/00
(52) U.S. Cl. .................. 435/255.1; 426/62; 435/317.1; 435/820; 435/822
(58) Field of Search ................ 435/255.1, 317.1, 435/820, 822; 426/62

(56) References Cited

U.S. PATENT DOCUMENTS

| | | | |
|---|---|---|---|
| 3,961,080 | 6/1976 | Sugimoto et al. | 426/60 |
| 3,975,553 | 8/1976 | Griffon | 426/656 |
| 4,079,048 | 3/1978 | Chao | 260/112 R |
| 4,122,196 | 10/1978 | Robbins et al. | 426/60 |
| 4,313,966 | 2/1982 | Basa et al. | 426/250 |
| 4,574,086 | 3/1986 | Shackelford | 426/62 |
| 4,765,992 | 8/1988 | Geneix et al. | 426/15 |
| 4,810,646 | 3/1989 | Jamas et al. | 435/101 |
| 4,962,094 | 10/1990 | Jamas et al. | 514/54 |
| 4,976,982 | 12/1990 | Gillmore et al. | 426/557 |
| 4,996,063 * | 2/1991 | Inglett | 426/21 |
| 5,250,436 | 10/1993 | Jamas et al. | 435/255.2 |
| 5,458,893 * | 10/1995 | Smith | 426/18 |

FOREIGN PATENT DOCUMENTS

| | | |
|---|---|---|
| 0415 788 A1 | 8/1990 | (EP) . |
| 0474 347 A1 | 3/1992 | (EP) . |

OTHER PUBLICATIONS

Database WPI, Section Ch, Week 7949, Derwent Publications Ltd. AN 79–88295B & JP–A–54 138 115 (abstract).

Database WPI, Section Ch, Week 791749, Derwent Publications Ltd. AN 79–32367B & JP–A–54 035 249 (abstract).

Gourbrere et al., "Microscopy of the Mycoflora of Fir Abies–Alba Needles III. Marasmius–Androsaceus", Can. J. Bot 65(1), 1987 (abstract).

\* cited by examiner

*Primary Examiner*—Deborah K. Ware
(74) *Attorney, Agent, or Firm*—Norris, McLaughlin & Marcus

(57) ABSTRACT

The present invention provides a coloring agent comprising glucan-containing yeast cell ghosts which comprise a proportion of substantially intact yeast cell walls and at least one color source. The color source is selected to give the desired color in the coloring agent and in any product in which the coloring agent is used and may be any dye or pigment. For uses such as in foodstuffs, pharmaceuticals and cosmetics, the coloring agents must be acceptable for food and/or pharmaceutical use.

3 Claims, 2 Drawing Sheets

YEAST DEBRIS PRODUCTS

This application is a divisional of case Ser. No. 08/470,386, filed Jun. 6, 1995, now U.S. Pat. No. 5,686,296, which is a divisional of case Ser. No. 08/047,726, filed Apr. 15, 1993, now U.S. Pat. No. 5,545,557.

BACKGROUND OF THE INVENTION

1. Field of the Invention

This invention relates to the use of yeast cell debris products in foodstuffs; cosmetics and pharmaceuticals.

2. Description of Related Art

Yeast extract is commercially produced on a large scale by lysis (e.g., hydrolysis, autolysis or plasmolysis) of baker's yeast or brewer's yeast in suitable form or of other fermentation yeasts (e.g., from gasohol production), which results in soluble material and material which is rich in virtually intact cell wall bodies. The latter material is normally removed from the soluble material by centrifugation. The lysis inevitably results in some disruption of the cell walls, such that there is a substantial proportion of virtually intact cell wall bodies, with at least one zone of discontinuity in the cell wall surface region (that is, holes have resulted in the relevant cell walls). The material containing cell wall bodies (known as yeast debris, or colloquially as yeast ref), which has a dark brown color, an unpleasant odor and rapidly putrifies, contains a number of undesirable materials, such as trace elements, coloring agents, hop extracts, tartrates, microorganisms, bacteria, protein slime and a large amount of insoluble components such as yeast cell wall bodies, as well as a certain amount of unlysed whole cells; such yeast debris is normally discarded. The soluble material from which the debris has been separated is normally used for the extraction of useful materials, such as yeast extract.

PCT/GB91/01819 discloses a process of treating yeast debris which produces a purified form of yeast ghosts or shells having substantially intact cell walls (that is, retaining the in vivo morphology of yeast cell walls in yeast debris), but without the yeast cell contents. That is, the yeast ghosts correspond in morphology to that of lysed material (the yeast debris, or ref) and not that of the whole yeast cells; the yeast ghosts comprise essentially yeast beta-glucan.

Yeast beta-glucans are, of course, well known. U.S. Pat. No. 4,810,646 discloses a method of producing yeast beta-glucans, which comprises separating growing *Saccharomyces cerevisiae* yeast from its growth medium, subjecting the intact whole yeast cells to alkaline digestion to solubilize the protein portion of the cell, and treating the insoluble glucan with acetic acid to alter the beta (1,6) linkages. The resulting whole glucan particles are described in U.S. Pat. No. 4,962,094 as being suitable for use as dietary additives and are said to substantially retain the in vivo glucan three-dimensional molecular structure of the yeast cells from which they are derived. However, the cell walls are effectively destroyed in the method described. In PCT/GB91/01819, the yeast ghosts or shells are obtained from yeast debris without destruction of the cell wall structure.

The term yeast cell ghosts, as used herein, covers yeast ghosts or shells having a proportion of yeast cell wall which is substantially intact.

The present invention is based on applications of the yeast cell ghosts described in PCT/GB91/01819.

It has been found that yeast cell ghosts may be used to produce coloring agents which are insoluble in aqueous media. The coloring agents may be produced from natural substances thus avoiding the use of artificial carriers and/or colorings. The coloring agents may be used in impart color to a variety of materials including foodstuffs, cosmetics and pharmaceuticals.

SUMMARY OF THE INVENTION

Accordingly, the present invention provides a coloring agent comprising glucan-containing yeast cell ghosts which comprise a proportion of substantially intact yeast cell walls and at least one color source. The color source is selected to give the desired color in the coloring agent and in any product in which the coloring agent is used and may be any dye or pigment. For uses such as in foodstuffs, pharmaceuticals and cosmetics, the coloring agents must be acceptable for food and/or pharmaceutical use. Preferably, the color sources are either naturally occurring or are provided by naturally occurring products such as turmeric and annatto. The color sources may be partly or fully purified from their natural source or used without purification.

The present invention also provides a process for producing a coloring agent comprising the steps of:

(1) providing an aqueous mixture of at least one color source and yeast cell ghosts which comprise a proportion of substantially intact yeast cell walls;

(ii) separating insoluble solids from the mixture; and (iii) drying the insoluble solids.

The aqueous mixture may be treated to optimize the formation of the coloring agent e.g., by adjusting the pH of the mixture.

DETAILED INVENTION

Figure 1:
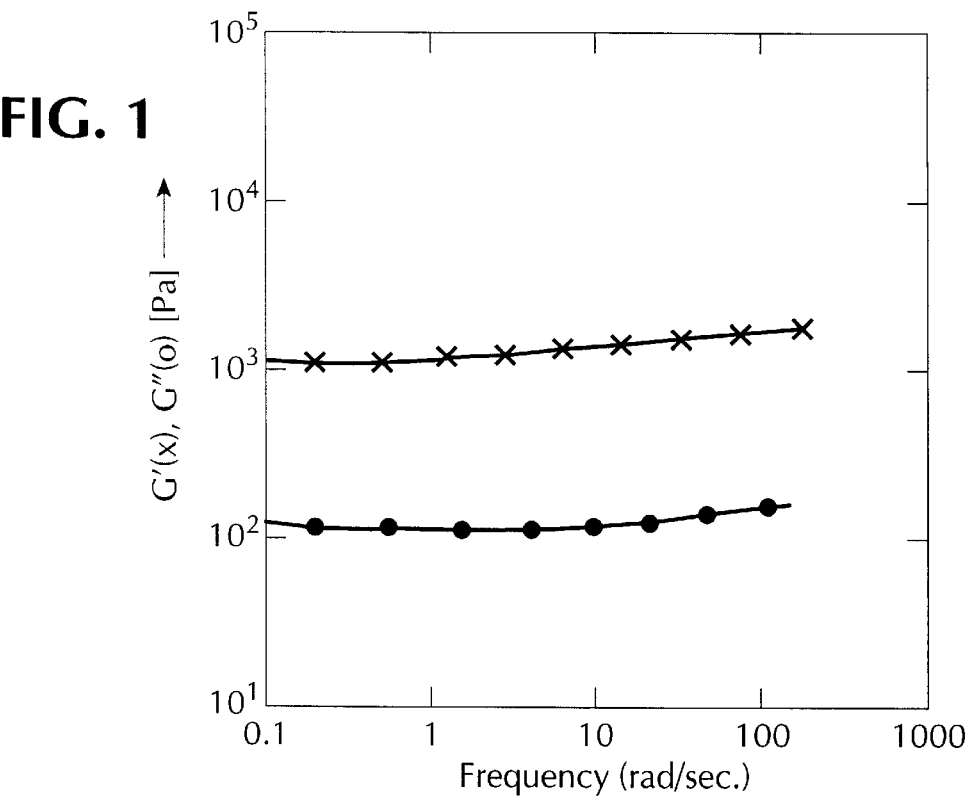
FIG. 1 shows the storage and loss moduli of yeast cell ghosts as a function of the frequency of oscillatory deformation.

Preferably, the aqueous mixture is formed by first adding at least one color source and subsequently adding yeast cell ghosts to water or another suitable aqueous solution. The mixture may be stirred for at least 30 seconds, preferably for 30 seconds to 5 minutes (e.g., 1 minute). The insoluble solids may be separated from the aqueous mixture in any one of a number of ways well known to those skilled in the art e.g., by centrifugation. The insoluble solids are preferably washed before drying preferably with water. The insoluble solids may be dried in a number of ways e.g., by freeze drying.

The coloring agents of the present invention may be used to provide color in foodstuffs, cosmetics and pharmaceutical compositions said pharmaceutical compositions further comprise a pharmaceutically active substance.

Yeast cell ghosts for use in the present invention may be produced by the process of treating yeast debris having a solids content not exceeding 20% by weight which is disclosed in PCT/GB91/01819 and which comprises:

(a) extracting said debris with a food grade alkaline salt;

(b) separating whole cells from the extracted debris so as to leave a material rich in disrupted but otherwise intact cell walls;

(c) treatment of the latter material with an alkaline extraction agent;

(d) bleaching said material with a bleaching agent or food grade oxidizing/reducing agent (such as ascorbic acid) either before or after said separation step; and (e) lowering the pH of said bleached material using a food grade acid (such as citric acid, orthophosphoric acid, dilute hydrochloric acid or dilute sulphuric acid).

Typical food grade alkaline salts for use in step (a) include sodium, calcium or potassium bicarbonate, or sodium, calcium or potassium carbonate; sodium bicarbonate is most preferred. The yeast debris typically has a solids content of about 2 to 12%, such as 4 to 8% (generally about 5%) by weight and a viscosity in the range of about 5–15 cP (5% aqueous suspension). The debris is generally extracted in step (a) of the process according to the invention with the alkaline salt, generally at substantially ambient temperatures for approximately one hour. The alkaline salt (which, as previously mentioned, is preferably sodium bicarbonate) is preferably used in an amount of up to 2.5% (preferably about 1%) weight, based on the total volume of yeast debris (liquids and solids) and preferably such that the resulting extracted mix has a pH in the range 8 to 12, more preferably about 8 to 9.

The separation of whole cells from the extracted debris so as to produce material rich in disrupted cell walls is generally carried out by mechanical methods, of which centrifugation is preferred. The centrifugation is typically operated at about 5,000 rpm for differential centrifugation or about 2,500 rpm for static centrifugation. The use of a bicarbonate in stage (a) has been found to assist the separation stage (possibly because of gas evolution which serves to make the yeast cell ghosts lighter).

Following separation, the material is treated with an alkaline extraction and extraction agent such as potassium hydroxide, sodium hydroxide or calcium hydroxide. This treatment with an alkaline extraction agent (which is similar to the process known as mercerisation) typically involves treatment in an alkaline solution having a pH of 8 to 14, preferably about 12 to 12.5. The treatment assists in removing colored products, dissolving unwanted materials such as protein, opening up the structure of the cell walls and facilitating the bleaching step. The mixture is then preferably heated to a temperature in the range of about 65° to 85° C. for at least one hour. If the final product is required to have a pale cream color, it is preferred that the alkali used comprises potassium or sodium hydroxide; however if the final product is required to have a white color it is preferred that the alkali used comprises calcium hydroxide.

The bleaching stage is preferably carried out using hydrogen peroxide or a food-grade oxidizing/reducing agent (such as ascorbic acid) when the product is to be used for food purposes; the bleaching is preferably carried out such that the bleached material is pale cream or white in color. The bleaching stage is preferably carried out in a reactor and the quantity of material rich in disrupted cell walls introduced into the reactor is preferably monitored such that the material occupies not more than about half of the reactor volume. This is because the bleaching stage typically involves foaming which causes a substantial increase in the volume of the material being treated. Preferably the foaming is substantially controlled using a foam breaking paddle and can be substantially lessened by the addition of anti-foaming agents.

Optionally the bleached material may be treated with a food grade acid (typically hydrochloric or orthophosphoric acid), centrifuged and treated with lecithin. The material may then be further centrifuged prior to drying. Treatment of the bleached material with lecithin is advantageous because lecithin helps to mask any residual flavor or odor pertaining to the yeast debris.

The lowering of the pH with the food grade acid may be carried out by washing the material being centrifuged, or may be carried out subsequently. The pH is generally lowered to a pH of 5 to 6, either in a single stage, or by lowering initially to a value from about 6 to 7.5 (such as about 7.0) and at a later stage to pH about 5 to 6.

Yeast cell ghosts may also be produced by the improved process of the present invention which provides a process for processing yeast cell ghosts which effects greater de-flavoring and de-coloring than previous processes.

Accordingly, the invention provides a process for preparing yeast cell ghosts which comprise at least a proportion of substantially intact yeast cell walls which comprises the steps of:

(i) extracting yeast debris having a solids content not exceeding 20% by weight with acid;

(ii) treating the extracted debris with an alkali;

(iii) separating whole cells from the treated mixture so as to leave a material rich in disrupted but otherwise intact cell walls;

(iv) bleaching said material with a bleaching agent or food grade oxidizing/reducing agents (such as ascorbic acid) after said separation step; and, optionally, (v) lowering the pH of said bleached material using a food grade acid (such as citric acid, dilute hydrochloric acid or dilute sulphuric acid).

The yeast debris used in step (i) typically has a solids content of about 2 to 10%, such as 4 to 8% (e.g., about 5%) by weight and a viscosity in the range of about 5–15 cP (5% aqueous suspension). The debris is generally extracted at 50–100° C. (e.g., 60–70° C.) for 30 minutes to 2 hours (e.g., 1 hour). Many acids may be used in the process (e.g., hydrochloric sulphuric, phosphoric and citric acids) either alone or as a mixture of two or more acids. The acid is present at a concentration effective to carry out step (i). Ascorbic acid is preferably used in an amount of up to 2.5% preferably 0.5 to 1% (e.g., 1%) by weight based on the total volume of yeast debris (liquids and solids) and is preferably added as a solid. Ascorbic acid effects both partial hydrolysis and partial oxidation of the yeast debris.

The alkali treatment in step (ii) may be carried out with an inorganic alkali such as potassium hydroxide, sodium hydroxide or calcium hydroxide. The treatment is typically carried out in an alkaline solution having a pH of 8 to 14, preferably about 12 to 12.5. The yeast debris mixture is preferably diluted to from 1 to 5% (e.g., from 2. to 3%) w/v prior to treatment. The mixture is heated to 65° to 85° C. for 30 minutes to 2 hours (e.g., about 1 hour). Step (ii) is thus complete in a shorter time than the corresponding step in the known process. If the final product is required to have a pale cream color, it is preferred that the alkali used comprises potassium or sodium hydroxide; however if the final product is required to have a white color it is preferred that the alkali used comprises calcium hydroxide.

The separation of whole cells from the extracted debris so as to produce material rich in disrupted cell walls (step (iii)) is generally carried out by mechanical methods, of which centrifugation is preferred. The centrifuge is typically operated at about 5,000 rpm for differential centrifugation or about 2,500 rpm for static centrifugation. Preferably the alkalinity is reduced (but preferably not below pH 9.5) prior to centrifugation.

The bleaching stage (step (iv)) is preferably carried out using hydrogen peroxide or a food-grade oxidizing/reducing agent (such as ascorbic acid) when the product is to be used for food purposes; the bleaching is preferably carried out such that the bleached material is pale cream or white in color, which is advantageous when the resulting product is intended for use as a food grade material such as functional fibre. The bleaching stage is preferably carried out in a reactor and the quantity of material rich in disrupted cell walls introduced into the reactor is preferably monitored such that the material occupies not more than about half of the reactor volume. This is because the bleaching stage typically involved foaming which causes a substantially increase in the volume of the material being treated. Preferably for foaming is substantially controlled using a foam breaking paddle and can be substantially lessened by the addition of anti-foaming agents.

The bleached product may be further treated by neutralization with ascorbic acid (preferably as a concentrated aqueous solution), centrifugation and washing.

The process of the invention provides a yeast cell ghost product having less flavor and a lighter color than previous processes.

In another aspect, the present invention provides a no-fat dressing which comprises yeast cell ghosts.

Substitution of fats by low calorie formulations which impart fat-like texture properties has been achieved by using polysaccharides in foodstuffs. In most cases, however, polysaccharides only partly substitute for fats to produce lower-fat "Lite" products. Additionally, some of the polysaccharides used are chemically modified or are derived from sources which are not considered "natural" and must thus undergo extensive trials before use.

The invention provides a no-fat product comprising yeast cell ghosts and, therefore, contains a fat substitute which has undergone a minimum of chemical modification (solubilization of part of the structure and at least partial oxidation). Yeast cell ghosts, in their hydrated form (5–10% w/v) are effective substitutes for oil in foodstuffs since the Theological and textural properties of the mixture may be made to be similar to those of fats. The yeast cell ghosts are indigestible and thus a virtually calorie-free dietary fibre.

Accordingly, the present invention provides a no-fat dressing comprising from 1 to 20% w/v of yeast cell ghosts which comprise a proportion of substantially intact yeast cell walls and from 50 to 95% w/v of water. Preferably, the no-fat dressing comprises from 1 to 10% (e.g., 2 to 8%) w/v of yeast cell ghosts and 60 to 90% (e.g., 70–85%) w/v of water. The no-fat dressings of the invention may also contain one or more of (i) from 0 to 20%, preferably from 0 to 10% (e.g., 1 to 5%) w/v of vinegar; (ii) from 0 to 10%, preferably 0 to 5% (e.g., 0.5 to 2%) w/v of salt; (iii) from 0 to 10%, preferably from 0 to 5% (e.g., 0.5 to 5%) w/v of sucrose; (iv) from 0 to 10%, preferably from 0 to 1% (e.g., up to 0.5%) w/v of xanthan gum; and (v) from 0 to 5%, preferably from 0 to 2% (e.g., up to 1%) w/v potassium sorbate.

The no-fat dressings may also contain other additives (e.g., flavorings or egg white). The dressings may be prepared by standard methods known to those skilled in the art. In one method of preparing the no-fat dressings of the invention, the dry ingredients are mixed together in a pan and the water and vinegar added. The mixture is then heated to 90°° C. and held at this temperature for 30 seconds. The mixture is cooled to 20° C. and the pan and its contents reweighed. Loss in weight due to evaporation is corrected for by the addition of water. The egg yolk is added gradually to the starch paste while mixing with a high-shear mixer. Mixing is continued for 3 minutes after the last of the oil and egg has been added. A highly acceptable dressing is obtained which has a good shelf life when stored at 4° C. in sterile jars.

The no-fat dressings of this invention exhibit good lipomimetic and rheological properties.

FIG. 1 shows the storage and loss moduli ($G^1$ and $G^{11}$ respectively) of yeast ghost cells from brewer's yeast as a function of the frequency of oscillatory deformation.

In this profile, the solid-like characteristics (represented by $G^1$) predominate over liquid-like response (loss modulus $G^{11}$) and both moduli show only slight variation with frequency. This is the behavior typical of a gel.

Figure 2:
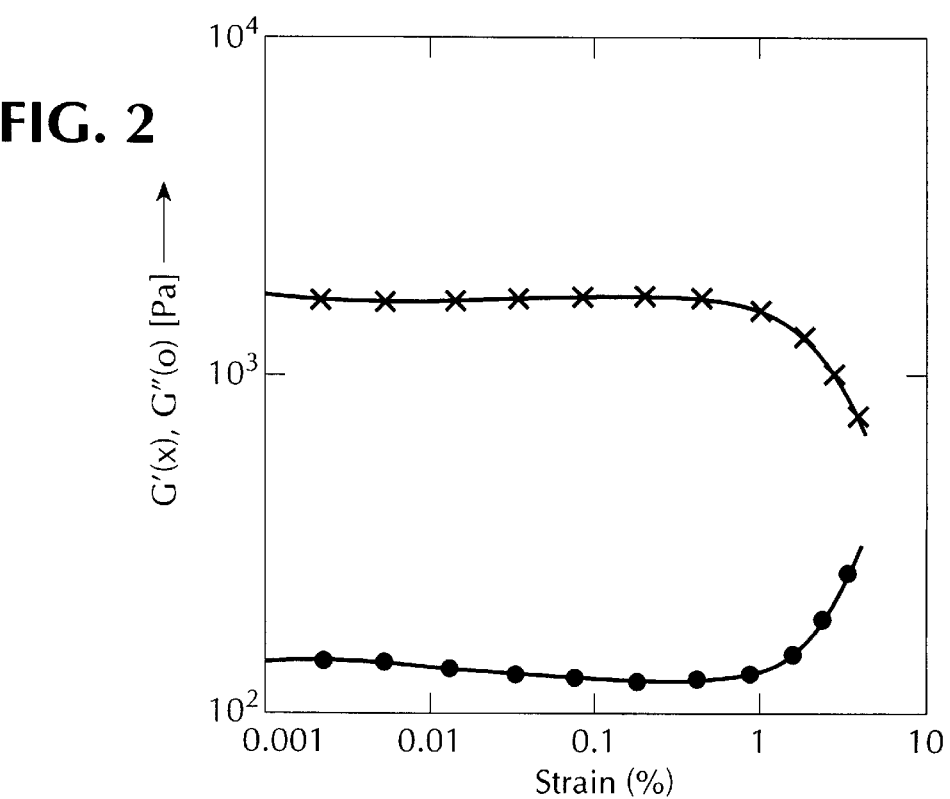
FIG. 2 shows the storage and loss moduli of yeast cell ghosts as a function of Strain.

FIG. 2 shows the same moduli as a function of Strain, the solid-like characteristics are seen to break-down at about 2% strain. After disturbance by applied stress, the solid-like characteristics slowly return over time. This combination of solid-like properties at rest and liquid-like properties under applied stress (weak gel behavior) provides solutions that can be pumped or poured but are capable of stabilizing emulsions over a long period of time. These properties (lipomimetry) are weak for spreads (especially mayonnaise-type products) and the thixotropic properties of mayonnaise have been documented. Similar properties are exhibited by yeast cell ghosts prepared from other sources of yeast.

Figure 3:
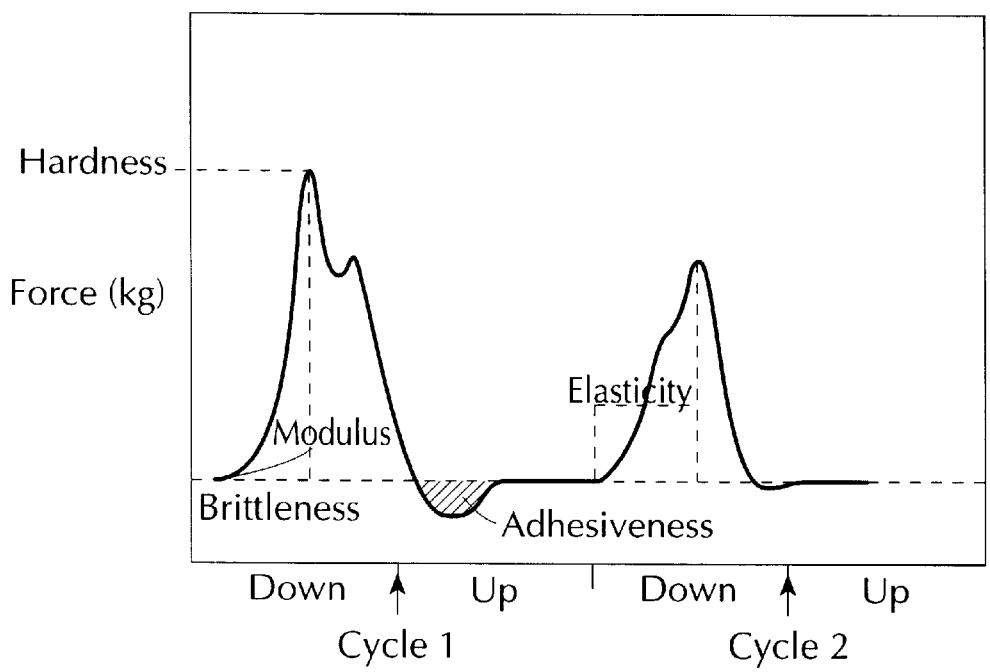
FIG. 3 shows an idealized texture profile for a gel.
Figure 4:
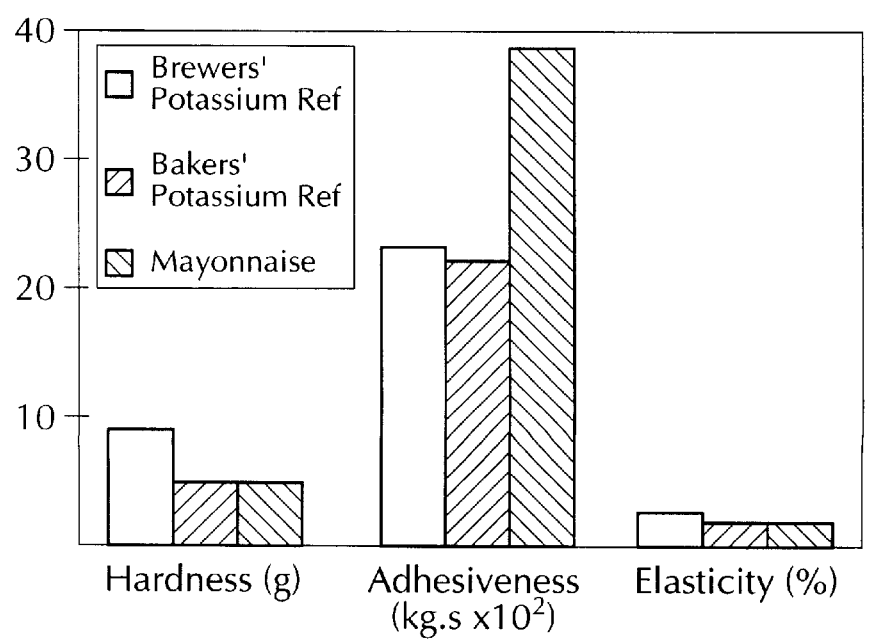
FIG. 4 shows hardness, adhesiveness and elasticity comparisons for brewers' and bakers' potassium "ref" and mayonnaise.

The texture profiles of preparations of 8% aqueous suspensions of brewer's and bakers' potassium ref (i.e., yeast cell ghosts prepared from brewer's and bakers' yeast by extraction using potassium salts) and mayonnaise (sold under the registered trade mark HELLMANN'S) were compared using an Instron "Two Bite" Texture Profile Analyzer. Three parameters were considered (a) hardness as the maximum force (kg) occurring at any time during the first compression cycle, (b) adhesiveness as the force preventing withdrawal of the compression plate (arbitrary units) and (c) elasticity as the degree to which the sample returned to its original shape (%). An idealized texture profile for a gel such as a lipomimetic) is shown in FIG. 3. Comparison of the three parameters measured for brewers' and bakers' potassium "ref" and mayonnaise is shown in FIG. 4. The weak gel characteristics are demonstrated by these Theological tests, breaking-down under weak strain (indicative of spreadability). The similarities observed in the texture profiles clearly show the suitability of these products in spreads and dressings. Such results correlate well with perceived texture and "mouth-feel".

The following are examples of the present invention, and not meant to be limiting in any way.

EXAMPLE 1

Brewer's yeast was subjected to autolysis, for breaking up of the cell membranes. The lysed product was then separated by centrifugation to produce yeast debris the fraction containing the cell bodies having a viscosity of 10 cP (5% aqueous solution).

The yeast debris was then treated with sodium bicarbonate to as to produce an extracted mix having a pH of 8.5. The mix was then stirred for about one hour at room temperature, and centrifuged for further separation.

The centrifuged material resulted in two streams namely cell wall rich material and undegraded cells. The cell wall rich material was resuspended in 2.5% sodium hydroxide and then 40% sodium hydroxide added so as to adjust the pH of one material to 12.5. The cell wall rich material was then indirectly heated on a water bath to about 65° C. for about one hour and then bleached by treatment with hydrogen peroxide, for about one hour with mixing. Concentrated hydrochloric acid was then added to the bleached material so as to achieve a pH of 7.0; the material was further centrifuged and the pH further lowered to 5.0. The resulting product was substantially free of any whole yeast cells and predominantly comprised yeast ghosts or shells having substantially uncollapsed walls. The yeast ghosts confined a lower quantity of yeast cell contents relative to the whole cells of the debris.

Water (200 ml) was acidified to pH 2 with dilute hydrochloric acid and turmeric (0.3 g) added to the resulting solution. The yeast cell ghosts (8.0 g) were added to the solution and the mixture stirred for one minute, centrifuged, washed twice with water and freeze-dried to give a stable canary yellow lake.

EXAMPLE 2

Water (200 ml) was acidified to pH 6 with dilute hydrochloric acid and annatto (0.3 g) added to the resulting solution. Yeast cell ghosts (8.0 g) as prepared in Example 1 were added to the solution and the mixture stirred for 1 minute, centrifuged, washed twice with water and freeze-dried to give a stable orange lake.

What is claimed is:

1. A fat substitute comprising yeast cell ghosts in hydrated form having 5 to 10% w/v of said yeast cell ghosts wherein said yeast cell ghosts have the in vivo morphology of yeast cell walls consisting essentially of yeast beta-glucan and there is no destruction of the cell wall structure of said yeast cell ghosts.

2. A no-fat dressing composition which comprises from 1 to 10% w/v of yeast cell ghosts in hydrated form having 5 to 10% w/v of said yeast cell ghosts and the in vivo morphology of yeast cell walls consisting essentially of yeast beta-glucan and from 60 to 90% w/v water, wherein there is no destruction of the cell wall structure of said yeast cell ghosts.

3. The no-fat dressing composition of claim 2, which further comprises up to 20% w/v vinegar, up to 10 % w/v salt, up to 10% w/v sucrose, up to 10% w/v xanthan gum and up to 5% w/v potassium sorbate.

* * * * *